(12) United States Patent
Gindele et al.

(10) Patent No.: US 9,731,112 B2
(45) Date of Patent: Aug. 15, 2017

(54) IMPLANTABLE ELECTRODE ASSEMBLY

(76) Inventors: Paul J. Gindele, Buffalo, MN (US); Brian P. Watschke, Minneapolis, MN (US)

( * ) Notice: Subject to any disclaimer, the term of this patent is extended or adjusted under 35 U.S.C. 154(b) by 174 days.

(21) Appl. No.: 14/343,276

(22) PCT Filed: Aug. 28, 2012

(86) PCT No.: PCT/US2012/052602
§ 371 (c)(1),
(2), (4) Date: Mar. 6, 2014

(87) PCT Pub. No.: WO2013/036399
PCT Pub. Date: Mar. 14, 2013

(65) Prior Publication Data
US 2014/0228922 A1    Aug. 14, 2014

Related U.S. Application Data
(60) Provisional application No. 61/532,277, filed on Sep. 8, 2011.

(51) Int. Cl.
*A61N 1/05*    (2006.01)
*A61N 1/36*    (2006.01)

(52) U.S. Cl.
CPC .............. *A61N 1/05* (2013.01); *A61N 1/0514* (2013.01); *A61N 1/36007* (2013.01); *A61N 1/36071* (2013.01); *A61N 1/36107* (2013.01)

(58) Field of Classification Search
CPC ..... A61N 1/05; A61N 1/0514; A61N 1/36007
See application file for complete search history.

(56) References Cited

U.S. PATENT DOCUMENTS

| | | | |
|---|---|---|---|
| 2,816,997 A | 12/1957 | Conrad | |
| 3,628,538 A | 12/1971 | Vincent et al. | |
| 3,640,284 A | 2/1972 | De Langis | |
| 3,646,940 A | 3/1972 | Timm et al. | |
| 3,650,276 A | 3/1972 | Burghele et al. | |

(Continued)

FOREIGN PATENT DOCUMENTS

| | | |
|---|---|---|
| DE | 8506522.6 U1 | 6/1985 |
| EP | 0 245 547 A1 | 11/1987 |

(Continued)

OTHER PUBLICATIONS

EPO Communication from corresponding European Application No. 12756606.5, dated May 8, 2014.

(Continued)

*Primary Examiner* — William Levicky
(74) *Attorney, Agent, or Firm* — Brake Hughes Bellermann LLP

(57) ABSTRACT

An implantable electrode assembly configured to deliver electrical stimulation signals to tissue of a patient includes an implantable mesh comprising a plurality of electrically conductive wires. A plurality of electrodes are fastened to the electrically conductive wires. The electrodes include a stimulation surface and an electrically conductive path between the stimulation surface and the wire, to which the electrode is attached. In one embodiment, the plurality of electrodes each comprise first and second members that are fastened together around one of the electrically conductive wires.

18 Claims, 4 Drawing Sheets

(56) References Cited

U.S. PATENT DOCUMENTS

| | | | |
|---|---|---|---|
| 3,662,758 A | 5/1972 | Glover |
| 3,667,477 A | 6/1972 | Susset et al. |
| 3,831,588 A | 8/1974 | Rindner |
| 3,866,613 A | 2/1975 | Kenny et al. |
| 3,870,051 A | 3/1975 | Brindley |
| 3,926,178 A | 12/1975 | Feldzamen |
| 3,941,136 A | 3/1976 | Bucalo |
| 3,983,865 A | 10/1976 | Shepard |
| 3,983,881 A | 10/1976 | Wickham |
| 3,999,555 A | 12/1976 | Person |
| 4,010,758 A | 3/1977 | Rockland et al. |
| 4,023,562 A | 5/1977 | Hynecek et al. |
| 4,023,574 A | 5/1977 | Nemec |
| 4,030,509 A | 6/1977 | Heilman et al. |
| 4,044,774 A | 8/1977 | Corbin et al. |
| 4,106,511 A | 8/1978 | Erlandsson |
| 4,136,684 A | 1/1979 | Scattergood et al. |
| 4,139,006 A | 2/1979 | Corey |
| 4,153,059 A | 5/1979 | Fravel et al. |
| 4,157,087 A | 6/1979 | Miller et al. |
| 4,165,750 A | 8/1979 | Aleev et al. |
| 4,177,819 A | 12/1979 | Kofsky et al. |
| 4,222,377 A | 9/1980 | Burton |
| 4,222,385 A | 9/1980 | Backhouse |
| 4,290,420 A | 9/1981 | Manetta |
| 4,387,719 A | 6/1983 | Plevnik et al. |
| 4,402,328 A | 9/1983 | Doring |
| 4,406,288 A | 9/1983 | Horwinski et al. |
| 4,407,296 A | 10/1983 | Anderson |
| 4,414,986 A | 11/1983 | Dickhudt et al. |
| 4,431,001 A | 2/1984 | Hakansson et al. |
| 4,432,372 A | 2/1984 | Monroe |
| 4,457,299 A | 7/1984 | Cornwell |
| 4,492,233 A | 1/1985 | Petrofsky et al. |
| 4,515,167 A | 5/1985 | Hochman |
| 4,542,753 A | 9/1985 | Brenman et al. |
| 4,550,737 A | 11/1985 | Osypka |
| 4,556,061 A | 12/1985 | Barreras et al. |
| 4,568,339 A | 2/1986 | Steer |
| 4,569,351 A | 2/1986 | Tang |
| 4,571,749 A | 2/1986 | Fischell |
| 4,580,578 A | 4/1986 | Barsom |
| 4,585,005 A | 4/1986 | Lue et al. |
| 4,590,949 A | 5/1986 | Pohndorf |
| 4,602,624 A | 7/1986 | Naples et al. |
| 4,607,639 A | 8/1986 | Tanagho et al. |
| 4,614,395 A * | 9/1986 | Peers-Trevarton .. A61N 1/3752 29/881 |
| 4,628,942 A | 12/1986 | Sweeney et al. |
| 4,688,575 A | 8/1987 | Du Vall |
| 4,703,755 A | 11/1987 | Tanagho et al. |
| 4,730,389 A | 3/1988 | Baudino |
| 4,731,083 A | 3/1988 | Fischell |
| 4,735,205 A | 4/1988 | Chachques et al. |
| 4,739,764 A | 4/1988 | Lue et al. |
| 4,750,494 A | 6/1988 | King |
| 4,771,779 A | 9/1988 | Tanagho et al. |
| 4,785,828 A | 11/1988 | Maurer |
| 4,825,876 A | 5/1989 | Beard |
| 4,846,191 A | 7/1989 | Brockway et al. |
| 4,873,986 A | 10/1989 | Wallace |
| 4,878,889 A | 11/1989 | Polyak |
| 4,881,526 A | 11/1989 | Johnson et al. |
| 4,913,164 A | 4/1990 | Greene et al. |
| 4,941,874 A | 7/1990 | Sandow et al. |
| 5,013,292 A | 5/1991 | Lemay |
| 5,019,032 A | 5/1991 | Robertson |
| 5,037,488 A | 8/1991 | Wienand |
| 5,082,006 A | 1/1992 | Jonasson |
| 5,094,242 A | 3/1992 | Gleason et al. |
| 5,103,835 A | 4/1992 | Yamada et al. |
| 5,112,344 A | 5/1992 | Petros |
| 5,113,868 A | 5/1992 | Wise et al. |
| 5,144,948 A | 9/1992 | Anderson et al. |
| 5,184,619 A | 2/1993 | Austin |
| 5,186,170 A | 2/1993 | Varrichio et al. |
| 5,193,539 A | 3/1993 | Schulman et al. |
| 5,193,540 A | 3/1993 | Schulman et al. |
| 5,199,430 A | 4/1993 | Fang et al. |
| 5,201,865 A | 4/1993 | Kuehn |
| 5,207,103 A | 5/1993 | Wise et al. |
| 5,211,175 A | 5/1993 | Gleason et al. |
| 5,233,982 A | 8/1993 | Kohl |
| 5,235,980 A | 8/1993 | Varrichio et al. |
| 5,250,022 A * | 10/1993 | Chien .................. A61K 9/0009 604/20 |
| 5,285,781 A | 2/1994 | Brodard |
| 5,291,902 A | 3/1994 | Carman |
| 5,300,093 A | 4/1994 | Koestner et al. |
| 5,312,439 A | 5/1994 | Loeb |
| 5,314,458 A | 5/1994 | Najafi et al. |
| 5,324,316 A | 6/1994 | Schulman et al. |
| 5,324,323 A | 6/1994 | Bui |
| 5,324,324 A | 6/1994 | Vachon et al. |
| 5,324,326 A | 6/1994 | Lubin |
| 5,330,505 A | 7/1994 | Cohen |
| 5,330,507 A | 7/1994 | Schwartz |
| 5,344,439 A | 9/1994 | Otten |
| 5,358,514 A | 10/1994 | Schulman et al. |
| 5,366,493 A | 11/1994 | Scheiner et al. |
| 5,370,670 A | 12/1994 | Chancellor |
| 5,385,577 A | 1/1995 | Maurer et al. |
| 5,391,191 A | 2/1995 | Holmstrom |
| 5,405,367 A | 4/1995 | Schulman et al. |
| 5,411,538 A | 5/1995 | Lin |
| 5,411,548 A | 5/1995 | Carman |
| 5,417,226 A | 5/1995 | Juma |
| 5,423,329 A | 6/1995 | Ergas |
| 5,425,751 A | 6/1995 | Baeten et al. |
| 5,431,686 A | 7/1995 | Kroll et al. |
| 5,452,719 A | 9/1995 | Eisman et al. |
| 5,484,445 A | 1/1996 | Knuth |
| 5,486,201 A | 1/1996 | Canfield |
| 5,508,476 A | 4/1996 | Dickenson |
| 5,518,504 A | 5/1996 | Polyak |
| 5,520,606 A | 5/1996 | Schoolman et al. |
| 5,522,266 A | 6/1996 | Nicholson et al. |
| 5,562,717 A | 10/1996 | Tippey |
| 5,564,434 A | 10/1996 | Halperin et al. |
| 5,566,680 A | 10/1996 | Urion et al. |
| 5,568,815 A | 10/1996 | Raynes et al. |
| 5,569,351 A | 10/1996 | Menta et al. |
| 5,571,148 A | 11/1996 | Loeb et al. |
| 5,611,515 A | 3/1997 | Benderev et al. |
| 5,611,768 A | 3/1997 | Tutrone |
| 5,611,769 A | 3/1997 | Monroe |
| 5,634,462 A | 6/1997 | Tyler |
| 5,658,321 A | 8/1997 | Fayram et al. |
| 5,693,000 A | 12/1997 | Crosby et al. |
| 5,702,428 A | 12/1997 | Tippey et al. |
| 5,722,997 A | 3/1998 | Nedungadi et al. |
| 5,726,624 A | 3/1998 | Caffee et al. |
| 5,752,978 A | 5/1998 | Chancellor |
| 5,766,229 A | 6/1998 | Bornzin |
| 5,769,873 A | 6/1998 | Zadeh |
| 5,785,666 A | 7/1998 | Costello et al. |
| 5,803,897 A | 9/1998 | Mooreville et al. |
| 5,807,265 A | 9/1998 | Itoigawa et al. |
| 5,807,397 A | 9/1998 | Barreras |
| 5,824,027 A | 10/1998 | Hoffer et al. |
| 5,833,595 A | 11/1998 | Lin |
| 5,836,886 A | 11/1998 | Itoigawa et al. |
| 5,836,994 A | 11/1998 | Bourgeois |
| 5,842,478 A | 12/1998 | Benderev et al. |
| 5,851,226 A | 12/1998 | Skubitz et al. |
| 5,860,425 A | 1/1999 | Benderev et al. |
| 5,876,353 A | 3/1999 | Riff |
| 5,899,909 A | 5/1999 | Claren et al. |
| 5,902,331 A | 5/1999 | Bonner et al. |
| 5,927,282 A | 7/1999 | Lenker et al. |
| 5,931,864 A | 8/1999 | Chastain et al. |
| 5,954,761 A | 9/1999 | Machek et al. |
| 5,957,920 A | 9/1999 | Baker |
| 5,957,965 A | 9/1999 | Moumane et al. |

(56) References Cited

U.S. PATENT DOCUMENTS

| | | | |
|---|---|---|---|
| 5,963,097 | A | 10/1999 | Garachtchenko et al. |
| 5,969,591 | A | 10/1999 | Fung |
| 5,978,712 | A | 11/1999 | Suda et al. |
| 5,984,711 | A | 11/1999 | Woodward |
| 5,984,854 | A | 11/1999 | Ishikawa et al. |
| 6,002,964 | A | 12/1999 | Feler et al. |
| 6,006,135 | A | 12/1999 | Kast et al. |
| 6,019,729 | A | 2/2000 | Itoigawa et al. |
| 6,026,326 | A | 2/2000 | Bardy |
| 6,027,456 | A | 2/2000 | Feler et al. |
| 6,038,463 | A | 3/2000 | Laske et al. |
| 6,039,686 | A | 3/2000 | Kovac |
| 6,042,534 | A | 3/2000 | Gellman et al. |
| 6,051,017 | A | 4/2000 | Loeb et al. |
| 6,055,456 | A | 4/2000 | Gerber |
| 6,061,596 | A | 5/2000 | Richmond et al. |
| 6,078,840 | A | 6/2000 | Stokes |
| 6,104,955 | A | 8/2000 | Bourgeois |
| 6,104,960 | A | 8/2000 | Duysens et al. |
| 6,110,101 | A | 8/2000 | Tihon et al. |
| 6,128,531 | A | 10/2000 | Campbell-Smith |
| 6,128,536 | A | 10/2000 | Noack et al. |
| 6,129,658 | A | 10/2000 | Delfino et al. |
| 6,131,575 | A | 10/2000 | Lenker et al. |
| 6,135,945 | A | 10/2000 | Sultan |
| 6,141,594 | A | 10/2000 | Flynn et al. |
| 6,161,029 | A | 12/2000 | Spreigl et al. |
| 6,178,356 | B1 | 1/2001 | Chastain et al. |
| 6,185,452 | B1 | 2/2001 | Schulman et al. |
| 6,208,894 | B1 | 3/2001 | Schulman et al. |
| 6,221,024 | B1 | 4/2001 | Miesel |
| 6,238,423 | B1 | 5/2001 | Bardy |
| 6,240,315 | B1 | 5/2001 | Mo et al. |
| 6,240,316 | B1 | 5/2001 | Richmond et al. |
| 6,243,607 | B1 | 6/2001 | Mintchev et al. |
| 6,248,083 | B1 | 6/2001 | Smith et al. |
| 6,253,108 | B1 | 6/2001 | Rosborough et al. |
| 6,259,949 | B1 | 7/2001 | Rosborough et al. |
| 6,263,241 | B1 | 7/2001 | Rosborough et al. |
| 6,266,557 | B1 | 7/2001 | Roe et al. |
| 6,266,564 | B1 | 7/2001 | Hill et al. |
| 6,304,786 | B1 | 10/2001 | Heil et al. |
| 6,328,686 | B1 | 12/2001 | Kovac |
| 6,328,687 | B1 | 12/2001 | Karram et al. |
| 6,341,236 | B1 | 1/2002 | Osorio et al. |
| 6,354,991 | B1 | 3/2002 | Gross et al. |
| 6,356,788 | B2 | 3/2002 | Boveja et al. |
| 6,360,750 | B1 | 3/2002 | Gerber et al. |
| 6,366,814 | B1 | 4/2002 | Boveja et al. |
| 6,382,214 | B1 | 5/2002 | Raz et al. |
| 6,393,323 | B1 | 5/2002 | Sawan |
| 6,397,109 | B1 | 5/2002 | Cammilli et al. |
| 6,407,308 | B1 | 6/2002 | Roe et al. |
| 6,418,930 | B1 | 7/2002 | Fowler |
| 6,477,414 | B1 | 11/2002 | Silvian |
| 6,478,727 | B2 | 11/2002 | Scetbon |
| 6,505,074 | B2 | 1/2003 | Boveja |
| 6,505,082 | B1 | 1/2003 | Scheiner et al. |
| 6,572,543 | B1 | 6/2003 | Christopherson et al. |
| 6,582,441 | B1 | 6/2003 | He et al. |
| 6,585,660 | B2 | 7/2003 | Dorando et al. |
| 6,600,956 | B2 | 7/2003 | Maschino et al. |
| 6,612,977 | B2 | 9/2003 | Staskin et al. |
| 6,641,524 | B2 | 11/2003 | Kovac |
| 6,641,525 | B2 | 11/2003 | Rocheleau et al. |
| 6,648,921 | B2 | 11/2003 | Anderson et al. |
| 6,650,943 | B1 | 11/2003 | Whitehurst et al. |
| 6,652,449 | B1 | 11/2003 | Gross et al. |
| 6,652,450 | B2 | 11/2003 | Neisz et al. |
| 6,652,499 | B1 | 11/2003 | Edgren et al. |
| 6,654,643 | B1 * | 11/2003 | Schmid ............ H01R 4/2404 439/909 |
| 6,658,297 | B2 | 12/2003 | Loeb |
| 6,659,936 | B1 | 12/2003 | Furness et al. |
| 6,691,711 | B2 | 2/2004 | Raz et al. |
| 6,709,385 | B2 | 3/2004 | Forsell |
| 6,712,772 | B2 | 3/2004 | Cohen et al. |
| 6,735,474 | B1 | 5/2004 | Loeb et al. |
| 6,738,674 | B2 | 5/2004 | Osypka |
| 6,745,079 | B2 | 6/2004 | King |
| 6,764,472 | B1 | 7/2004 | Burke et al. |
| 6,802,807 | B2 | 10/2004 | Anderson et al. |
| 6,836,684 | B1 | 12/2004 | Rijkhoff et al. |
| 6,862,480 | B2 | 3/2005 | Cohen et al. |
| 6,885,894 | B2 | 4/2005 | Stessman |
| 6,896,651 | B2 | 5/2005 | Gross et al. |
| 6,911,003 | B2 | 6/2005 | Anderson et al. |
| 6,915,162 | B2 | 7/2005 | Noren et al. |
| 6,941,171 | B2 | 9/2005 | Mann et al. |
| 6,952,613 | B2 | 10/2005 | Swoyer et al. |
| 6,964,643 | B2 | 11/2005 | Hovland et al. |
| 6,964,699 | B1 | 11/2005 | Carns et al. |
| 6,971,393 | B1 | 12/2005 | Mamo et al. |
| 7,011,622 | B2 | 3/2006 | Kuyava et al. |
| 7,025,063 | B2 | 4/2006 | Snitkin et al. |
| 7,054,689 | B1 | 5/2006 | Whitehurst et al. |
| 7,070,556 | B2 | 7/2006 | Anderson et al. |
| 7,079,882 | B1 | 7/2006 | Schmidt |
| 7,120,499 | B2 | 10/2006 | Thrope et al. |
| 7,203,548 | B2 | 4/2007 | Whitehurst et al. |
| 7,212,867 | B2 * | 5/2007 | Van Venrooij ....... A61N 1/0534 607/116 |
| 7,217,237 | B2 | 5/2007 | Wassemann et al. |
| 7,231,259 | B2 * | 6/2007 | Jenney .................. A61N 1/056 607/116 |
| 7,267,645 | B2 | 9/2007 | Anderson et al. |
| 7,292,890 | B2 | 11/2007 | Whitehurst et al. |
| 7,303,525 | B2 | 12/2007 | Watschke et al. |
| 7,319,905 | B1 | 1/2008 | Morgan et al. |
| 7,328,068 | B2 | 2/2008 | Spinelli et al. |
| 7,330,764 | B2 | 2/2008 | Swoyer et al. |
| 7,343,202 | B2 | 3/2008 | Mrva et al. |
| 7,347,812 | B2 | 3/2008 | Mellier |
| 7,351,197 | B2 | 4/2008 | Montpetit et al. |
| 7,359,751 | B1 | 4/2008 | Erickson et al. |
| 7,376,467 | B2 | 5/2008 | Thrope et al. |
| 7,376,468 | B2 | 5/2008 | King et al. |
| 7,384,390 | B2 | 6/2008 | Furness et al. |
| 7,387,603 | B2 | 6/2008 | Gross et al. |
| 7,407,480 | B2 | 8/2008 | Anderson et al. |
| 7,412,289 | B2 | 8/2008 | Malonek et al. |
| 7,437,193 | B2 | 10/2008 | Parramon et al. |
| 7,450,987 | B2 | 11/2008 | Varrichio et al. |
| 7,500,945 | B2 | 3/2009 | Cox et al. |
| 7,565,198 | B2 | 7/2009 | Bennett et al. |
| 7,582,053 | B2 | 9/2009 | Gross et al. |
| 7,582,070 | B2 | 9/2009 | Goode et al. |
| 7,613,516 | B2 | 11/2009 | Cohen et al. |
| 7,628,795 | B2 | 12/2009 | Karwoski et al. |
| 7,647,113 | B2 | 1/2010 | Wirbisky et al. |
| 7,658,743 | B2 | 2/2010 | Ulmsten |
| 7,686,760 | B2 | 3/2010 | Anderson et al. |
| 7,715,920 | B2 | 5/2010 | Rondoni et al. |
| 7,725,197 | B2 | 5/2010 | Soltis et al. |
| 7,742,817 | B2 | 6/2010 | Malinowski et al. |
| 7,769,472 | B2 | 8/2010 | Gerber |
| 7,771,345 | B1 | 8/2010 | O'Donnell |
| 7,778,703 | B2 | 8/2010 | Gross et al. |
| 7,860,570 | B2 | 12/2010 | Whitehurst et al. |
| 7,890,176 | B2 | 2/2011 | Jaax et al. |
| 7,930,039 | B2 | 4/2011 | Olson |
| 8,019,443 | B2 | 9/2011 | Schleicher et al. |
| 8,052,731 | B2 | 11/2011 | Soltis et al. |
| 8,083,663 | B2 | 12/2011 | Gross et al. |
| 8,195,296 | B2 | 6/2012 | Longhini et al. |
| 2001/0002441 | A1 | 5/2001 | Boveja |
| 2001/0003799 | A1 | 6/2001 | Boveja |
| 2001/0018549 | A1 | 8/2001 | Scetbon |
| 2002/0022841 | A1 | 2/2002 | Kovac |
| 2002/0055761 | A1 | 5/2002 | Mann et al. |
| 2002/0062060 | A1 | 5/2002 | Gross et al. |
| 2002/0099259 | A1 | 7/2002 | Anderson et al. |
| 2002/0147382 | A1 | 10/2002 | Neisz et al. |
| 2002/0161382 | A1 | 10/2002 | Neisz et al. |

(56) References Cited

U.S. PATENT DOCUMENTS

| | | |
|---|---|---|
| 2002/0165566 A1 | 11/2002 | Ulmstein |
| 2003/0018365 A1 | 1/2003 | Loeb |
| 2003/0023296 A1 | 1/2003 | Osypka |
| 2003/0028232 A1 | 2/2003 | Camps et al. |
| 2003/0060868 A1 | 3/2003 | Janke et al. |
| 2003/0100930 A1 | 5/2003 | Cohen et al. |
| 2003/0144575 A1 | 7/2003 | Forsell |
| 2003/0171644 A1 | 9/2003 | Anderson et al. |
| 2003/0199961 A1 | 10/2003 | Bjorklund et al. |
| 2003/0212305 A1 | 11/2003 | Anderson et al. |
| 2003/0236557 A1 | 12/2003 | Whitehurst et al. |
| 2003/0236558 A1 | 12/2003 | Whitehurst et al. |
| 2004/0015057 A1 | 1/2004 | Rocheleau et al. |
| 2004/0015204 A1 | 1/2004 | Whitehurst et al. |
| 2004/0015205 A1 | 1/2004 | Whitehurst et al. |
| 2004/0039453 A1 | 2/2004 | Anderson et al. |
| 2004/0059392 A1 | 3/2004 | Parramon et al. |
| 2004/0068203 A1 | 4/2004 | Gellman et al. |
| 2004/0093053 A1 | 5/2004 | Gerber et al. |
| 2004/0152999 A1 | 8/2004 | Cohen et al. |
| 2004/0242956 A1 | 12/2004 | Scorvo |
| 2004/0248979 A1 | 12/2004 | Brettman et al. |
| 2005/0038489 A1 | 2/2005 | Grill |
| 2005/0043580 A1 | 2/2005 | Watschke et al. |
| 2005/0049648 A1 | 3/2005 | Cohen et al. |
| 2005/0055063 A1 | 3/2005 | Loeb et al. |
| 2005/0065395 A1 | 3/2005 | Mellier |
| 2005/0113877 A1 | 5/2005 | Spinelli et al. |
| 2005/0113881 A1 | 5/2005 | Gross et al. |
| 2005/0119710 A1 | 6/2005 | Furness et al. |
| 2005/0143618 A1 | 6/2005 | Anderson et al. |
| 2005/0149156 A1 | 7/2005 | Libbus et al. |
| 2005/0216069 A1 | 9/2005 | Cohen et al. |
| 2005/0228346 A1 | 10/2005 | Goode et al. |
| 2005/0245787 A1 | 11/2005 | Cox et al. |
| 2005/0245874 A1 | 11/2005 | Carrez et al. |
| 2005/0250977 A1 | 11/2005 | Montpetit et al. |
| 2005/0256367 A1 | 11/2005 | Banik |
| 2005/0277994 A1 | 12/2005 | McNamee et al. |
| 2005/0283235 A1 | 12/2005 | Kugler et al. |
| 2006/0004421 A1 | 1/2006 | Bennett et al. |
| 2006/0004429 A1 | 1/2006 | Mrva et al. |
| 2006/0135845 A1 | 6/2006 | Kuyava et al. |
| 2006/0149345 A1 | 7/2006 | Boggs, II et al. |
| 2006/0205995 A1 | 9/2006 | Browning |
| 2006/0241733 A1 | 10/2006 | Zhang et al. |
| 2006/0265027 A1 | 11/2006 | Vaingast et al. |
| 2006/0287571 A1 | 12/2006 | Gozzi et al. |
| 2007/0021650 A1 | 1/2007 | Rocheleau et al. |
| 2007/0027514 A1 | 2/2007 | Gerber |
| 2007/0043416 A1 | 2/2007 | Callas et al. |
| 2007/0100411 A1 | 5/2007 | Bonde |
| 2007/0123952 A1 | 5/2007 | Strother et al. |
| 2007/0179559 A1 | 8/2007 | Giftakis et al. |
| 2007/0185541 A1* | 8/2007 | DiUbaldi .............. A61N 1/0512 607/41 |
| 2007/0239224 A1 | 10/2007 | Bennett et al. |
| 2007/0253997 A1 | 11/2007 | Giftakis et al. |
| 2007/0253998 A1 | 11/2007 | Giftakis et al. |
| 2007/0255333 A1 | 11/2007 | Giftakis et al. |
| 2007/0255341 A1 | 11/2007 | Giftakis et al. |
| 2007/0260288 A1 | 11/2007 | Gross |
| 2008/0009914 A1 | 1/2008 | Buysman et al. |
| 2008/0033493 A1 | 2/2008 | Deckman et al. |
| 2008/0071321 A1 | 3/2008 | Boggs, II et al. |
| 2008/0109045 A1 | 5/2008 | Gross et al. |
| 2008/0114433 A1 | 5/2008 | Sage et al. |
| 2008/0132969 A1 | 6/2008 | Bennett et al. |
| 2008/0242918 A1 | 10/2008 | Gross et al. |
| 2008/0269548 A1 | 10/2008 | Vecchiotti et al. |
| 2009/0012592 A1 | 1/2009 | Buysman et al. |
| 2009/0036946 A1 | 2/2009 | Cohen et al. |
| 2009/0043356 A1 | 2/2009 | Longhini et al. |
| 2009/0096288 A1 | 4/2009 | Nguyen |
| 2009/0157091 A1 | 6/2009 | Buysman |
| 2009/0259280 A1 | 10/2009 | Wilkin et al. |
| 2009/0270941 A1* | 10/2009 | Mokelke .............. A61M 25/104 607/37 |
| 2010/0049289 A1 | 2/2010 | Lund et al. |
| 2010/0076254 A1 | 3/2010 | Jimenez et al. |
| 2010/0076255 A1 | 3/2010 | Robertson et al. |
| 2010/0114510 A1 | 5/2010 | Vaingast et al. |
| 2010/0160716 A1 | 6/2010 | Snow |
| 2010/0217340 A1 | 8/2010 | Watschke et al. |
| 2011/0015738 A1 | 1/2011 | Vaingast et al. |
| 2011/0270269 A1 | 11/2011 | Swoyer et al. |
| 2011/0301662 A1 | 12/2011 | Bar-Yoseph et al. |

FOREIGN PATENT DOCUMENTS

| | | |
|---|---|---|
| EP | 1 661 600 A1 | 5/2006 |
| EP | 1119314 B1 | 7/2006 |
| GB | 2 309 388 A | 7/1997 |
| JP | S52146088 | 12/1977 |
| JP | 2002521153 | 7/2002 |
| JP | 2003506145 | 2/2003 |
| JP | 2004515277 | 5/2004 |
| WO | 90/12617 A1 | 11/1990 |
| WO | 96/04955 A2 | 2/1996 |
| WO | 9632916 | 10/1996 |
| WO | 9817190 A2 | 4/1998 |
| WO | 0000082 A1 | 1/2000 |
| WO | 0001320 A2 | 1/2000 |
| WO | 0006246 A1 | 2/2000 |
| WO | 0019939 A1 | 4/2000 |
| WO | 0019940 A1 | 4/2000 |
| WO | 0110357 A1 | 2/2001 |
| WO | 01/47440 A2 | 7/2001 |
| WO | 0156499 A1 | 8/2001 |
| WO | 0172240 A1 | 10/2001 |
| WO | 0239890 A2 | 5/2002 |
| WO | 0245774 A2 | 6/2002 |
| WO | 02069781 A2 | 9/2002 |
| WO | 02/078592 A2 | 10/2002 |
| WO | 03/002192 A1 | 1/2003 |
| WO | 03002192 A1 | 1/2003 |
| WO | 03/094693 A2 | 11/2003 |
| WO | 2004047914 A1 | 6/2004 |
| WO | 2005122954 A1 | 12/2005 |
| WO | 2006014971 A2 | 2/2006 |
| WO | 2006047833 A1 | 5/2006 |
| WO | 2006126201 A2 | 11/2006 |
| WO | 2007025354 A1 | 3/2007 |
| WO | 2007056384 A2 | 5/2007 |
| WO | 2007097994 A2 | 8/2007 |
| WO | 2007106303 A2 | 9/2007 |
| WO | 2007126632 A3 | 11/2007 |
| WO | 2007145913 A1 | 12/2007 |
| WO | 2008057261 A2 | 5/2008 |
| WO | 2008111078 A2 | 9/2008 |
| WO | 2008121109 A1 | 10/2008 |
| WO | 2008130530 A1 | 10/2008 |
| WO | 2008150941 A2 | 12/2008 |
| WO | 2009026078 A2 | 2/2009 |
| WO | 2009094431 A2 | 7/2009 |
| WO | 2010107751 A2 | 9/2010 |
| WO | 2010107900 A2 | 9/2010 |
| WO | 2011143572 A1 | 11/2011 |
| WO | 2013036399 A2 | 3/2013 |

OTHER PUBLICATIONS

International Search Report and Written Opinion from PCT/US2007/004474, mailed Feb. 20, 2008.
International Search Report and Written Opinion from PCT/US2011/036455, mailed Oct. 18, 2011.
International Search Report and Written Opinion from PCT/US2012/052602, mailed Mar. 6, 2013.
Caldwell, K.P.S. "Electrical Stimulation.", Sphincter Research Unit, Royal Devon and Exeter Hospital, Exeter (England), Urol. Int. 29: 225, 1974.(1 page).

(56) References Cited

OTHER PUBLICATIONS

Caldwell, K.P.S. "The Use of Electrical Stimulation in Urinary Retention and Incontinence [Abridged]." Section of Urology, vol. 61, pp. 35-39, Jul. 1968.
Caldwell, K.P.S. et al. "Urethral Pressure Recordings In Male Incontinents Under Electrical Stimulation." Investigative Urology vol. 5, No. 6, pp. 572-579, May 1968.
Caldwell, K.P.S. et al. "Stress Incontinence in Females: Report on 31 Cases Treated by Electrical Implant." J. Obstet. Gynaec. Brit. Cwlth vol. 75, pp. 777-780, Jul. 1968.
Yamamoto et al., "Optimal parameters for effective electrical stimulation of the anal sphincters in a child with fecal incontinence: preliminary report," Pediatr Surg Int (1993) 8:132-137.
Yamanishi et al., "Electrical Stimulation for Stress Incontinence", Int. Urogynecol J (1998) 9:281-290 Springer-Verlag London Ltd.
Dietz et al., Mechanical Properties of Urogynecologic Implant Materials, Int. Urogynecol J. (2003) 14:239-243.
Iglesia et al., "The Use of Mesh in Gynecologic Surgery", Int. Urogynecol J. (1997) 8:105-115.
Merrill Daniel C. et al., "Treatment with Electrical Stimulation of the Pelvic Floor", Urology, Jan. 1975, vol. V, No. 1, pp. 67-72.
Chai et al., "Percutaneous Sacral Third Nerve Root Neurostimulation Improves Symptoms and Normalizes Urinary HG-EFG Levels and Antiproliferative Activity in Patients with Interstitial Cystitis", Urology, 55(5), pp. 643-646, May 2000.
Fall et al., "Electrical Stimulation in Interstitial Cystitis", Journal of Urology, 123(2), pp. 192-195, Feb. 1980.
Zermann et al., "Sacral Nerve Stimulation for Pain Relief in Interstitial Cystitis", Urol. Int., 65(2), pp. 120-121, 2000.
Caraballo et al., "Sacral Nerve Stimulation as a Treatment for Urge Incontinence and Associated Pelvic Floor Disorders at a Pelvic Floor Center: A Follow-up Study", Urology, 57(6 Suppl 1), p. 121, Jun. 2001.
P.D., O'Donnell ed., Urinary Incontinence, Chap. 26, 1997, Mosby Publishers, St. Louis, MO. pp. 197-2002.
Medtronic®'s "InterStim Therapy for Urinary Control-Patient Stories", 1997, Medtronic, Inc., Spring Lake Park, MN 2 pages.(http://webprod1.medtronic.com/neuro/interstim/4Bsize.html).
Summary of Safety and Effectiveness of Medtronic® InterStim® Sacral Nerve Stimulation(SNS)TM System, Sep. 1997, Medtronic, Inc., Spring Lake Park, MN, 2 pages.
Medtronic®'s "InterStim Therapy for Urinary . . . for People with Bladder Control Problem", 1997, Medtronic, Inc., Spring Lake Park, MN, 2 pages (http://webprod1.medtronic.com/neuro/interstim/1types.html).
Agazzi E. et al., "Percutaneous Tibial Nerve Stimulation and Short Latency Somatosensory Evoked Potentials: Preliminary Reports" Eur. Urol Suppl. 2007; 6(2): 141.
Arabi, K. et al., "Implantable Multiprogrammable Microstimulator Dedicated to Bladder Control", Med. & Biol. Eng. & Comput., 1996, 34, 9-12.
Bosch, J.L., "Electrical Neuromodularoty Therapy in Female Voiding Dysfunction", BJU Int. Sep. 2006; 98 Suppl 1:43-8; discussion 49. Review.
Bosch, J.L.H.R., "The Bion Device: A Minimally Invasive Implantable Ministimulator for Pudendal Nerve Neuromodulation in Patients with Detrusor Overactivity Incontinence", Urol. Clin. N. Am 32(2005) 109-112.
Bosch, J.L.H.R. et al., "The Long Term Effect of Electrostimulation of the Pelvic Floor on Painful Bladder Syndrome/Interstitial Cystitis Patients", Neurourology and Urodynamics 2008; 27(7 suppl).
Bresler, L. et al., "Effective Methods of Pelvic Plexus Nerve and Bladder Stimulation in Anesthetized Animal Model" J. Rehab. Res. & Dev. 49(4) 2008 627-638.
Brindley, G.S., "Electrolytic Current-Control Elements for Surgically Implanted Electrical Devices", Med. & Biol. Eng. & Comput., 1986, 24, 439-41.

Chai et al., "Modified Techniques of S3 Foramen Localization and Lead Implantation in S3 Neuromodulation", Urology 58: 786-790, 2001.
Diokno, A. et al., "A Simplified Method of Implanting a Neuromodulator Device" J. Urol. 169, 1466-69 2003.
Donaldson, N. et al., "Design of an Implant for Preventing Incontinence After Spinal Cord Injury", Artif Organs, vol. 32, No. 8, 2003.
Fall, M. et al., "Electrical Stimulation: A Physiologic Approach to the Treatment of Urinary Incontinence", Urologic Clinics of North America vol. 18 N. 2, May 1991 pp. 393-407.
Gaunt, R.A., "Control of Urinary Bladder Function with Devices: Successes and Failures", Prog Brain Res. 2006; 152: 163-94.
Green, R. et al., "Objective Methods for Evaluation of Interferential Therapy in the Treatment of Incontinence" IEEE Transactions on Biol. Eng. 37(6) 1990 615-623.
Grill, WM. et al., "Emerging Clinical Applicaitons of Electrical Stimulation: Opportunities for Restoration of Function" J Rehabiil Res Dev 20014 38(6); 651-53.
Herbison, GP. et al. "Sacral Neuromodulation with Implanted Devices for Urinary Storage and Voiding Dysfunction in Adults", The Cochrane Library 2009 issue 2 1-29 (31 pages).
Ishikawa, N. et al. "Development of a Non-Invasive Treatment System for Urinary Incontinence Using a Functional Continuous Magnetic Stimulator (FCMS)" Med. Biol. Eng. Comput., 1998, 36, 704-10.
Kirkham, APS. et al., "Neuromodulation Through Sacral Nerve Roots 2 to 4 with a Finetech-Brindley Sacral Posterior and Anterior Root Stimulator" Spinal Cord (2002) 40, 272-81.
Medtronic "Interstim® Therapy: Implant Manual" (32 pages) 2006.
Odagaki, M. et al., "Comparison of Current Distribution Based on Tissue Inhomogeneity in Magnetic Stimulation for Treatment of urinary Incontinece", IEEE Transactions on Magnetics, 41(10), 2005, 4155-57.
O'Riordan, J.M. et al., "Sacral Nerve Stimulation for Fecal Incontinence", Ir J Med Sci (2008) 177:117-119.
Petrofsky, J., "A Transurethral Electrical Stimulator", J. Clin. Eng. 17(2), 1992, 151-56.
Provost, B. et al., "Proposed New Bladder Volume Monitoring Device Based on Impedance Measurement", Med. Biol. Eng. Comput., 1997, 35, 691-694.
Sherman, N.D. et al., "Current and Future Techniques of Neuromodulation for Bladder Dysfunction", Curr Urol Rep. Nov. 8, 2007(6): 448-54.
Soumendra N. et al., "Sacral Neurostimulation for Urinary Retention: 10-Year Experience from One UK Centre", BJU International 101, 192-96 (2007).
Starkman, J. et al., "Refractory Overactive Bladder after Urethrolysis for Bladder Outlet Obstruction: Management with Sacral Neuromodulation", Int Urogynecol J (2008) 19:277-282.
Sutherland, S. et al., "Sacral Nerve Stimulation for Voiding Dysfunction: One Institution's 11-Year Experience", Neurourology and Urodynamics 26:19-28 (2007).
Washington, B. et al., "Implant Infection after Two-Stage Sacral Nerve Stimulator Placement", Int Urogynecol J (2007) 18:1477-1480.
Wenzel, B. et al., "Detecting the Onset of Hyper-Reflexive Bladder Contractions from the Electrical Activity of the Pudendal Nerve", IEEE Trans. Neural Sys. Rehab. Eng. 13(3) 2005 428-35.
White, W. et al., "Incidence and Predictors of Complications with Sacral Neuromodulation", Urology 73: 731-35, 2009.
Whiteside, J.L., "Lead Placement and Associated Nerve Distribution of an Implantable Periurethral Electrostimulatory", Int Urogynecol J Pelvic Floor Dysfunct. Mar. 20, 2009(3): 325-29.
Zonnevijlle, E. et al., "Dynamic Gracioplasty for Urinary Incontinence: The Potential for Sequential Closed-Loop Stimulation", Med. Eng. Phy. 25(2003) 755-63.

* cited by examiner

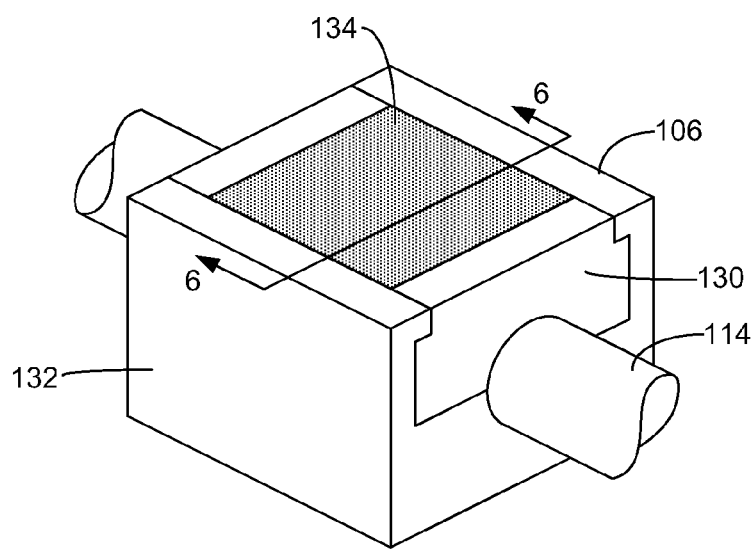
FIG. 6
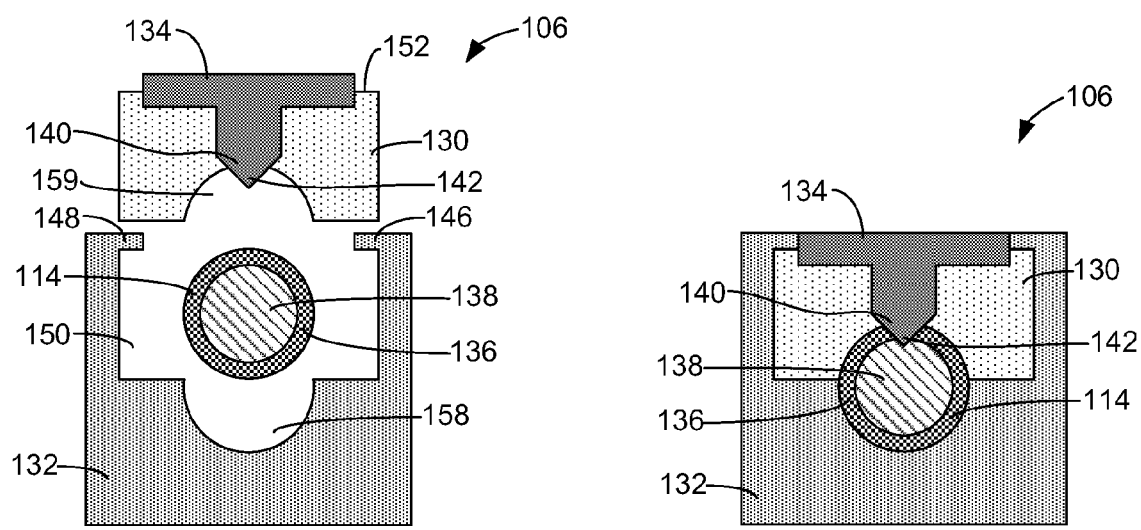
FIG. 7                                FIG. 8

IMPLANTABLE ELECTRODE ASSEMBLY

CROSS-REFERENCE TO RELATED APPLICATION

This Application is a Section 371 National Stage Application of International Application No. PCT/US2012/052602, filed Aug. 28, 2012 and published as WO 2013/036399 A2 on Mar. 14, 2013 in English, and claims the benefit of U.S. Provisional Application Serial No. 61/532,277, filed Sep. 8, 2011 under 35 U.S.C. §119(e). The contents of which are hereby incorporated by reference in their entirety.

BACKGROUND

Implantable electronic stimulator devices, such as neuromuscular stimulation devices, have been disclosed for use in the treatment of various pelvic conditions, such as urinary incontinence, fecal incontinence and sexual dysfunction. Such devices generally include one or more electrodes that are coupled to a control unit by electrode leads. A stimulation therapy is applied to the tissue through the electrode leads to treat the condition of the patient. Exemplary implantable electronic stimulator devices and uses of the devices are disclosed in U.S. Pat. Nos. 6,354,991, 6,652,449, 6,712,772 and 6,862,480, each of which is hereby incorporated by reference in its entirety.

The electrode leads typically include a tissue anchor, such as a helical coil or mesh. The primary objective of the tissue anchor is to prevent migration of the electrode lead within the tissue of the patient, as such movement may adversely affect the stimulation therapy.

SUMMARY

Embodiments of the invention are directed to an implantable electrode assembly that is configured to deliver electrical stimulation signals to tissue of a patient. In one embodiment, the implantable electrode assembly includes an implantable mesh comprising a plurality of electrically conductive wires. A plurality of electrodes are fastened to the electrically conductive wires. In one embodiment, the electrodes include a stimulation surface and an electrically conductive path between the stimulation surface and the wire, to which the electrode is attached. In one embodiment, the plurality of electrodes each comprise first and second members that are fastened together around one of the electrically conductive wires.

In accordance with another embodiment, the implantable electrode assembly comprises an implantable mesh including a plurality of tabs and a plurality of electrodes each fastened to one of the tabs.

Yet another embodiment of the invention is directed to a method, in which an implantable mesh comprising a plurality of electrically conductive wiress is provided. A plurality of electrodes are fastened to the electrically conductive wires. In one embodiment, the electrodes are fastened to the electrically conductive wires by mechanically fastening first and second members of each of the electrodes to one of the wires. A conductive path is formed between stimulation surfaces of the electrodes and the conductive wires responsive to the fastening of the electrodes to the wires.

This Summary is provided to introduce a selection of concepts in a simplified form that are further described below in the Detailed Description. This Summary is not indented to identify key features or essential features of the claimed subject matter, nor is it intended to be used as an aid in determining the scope of the claimed subject matter. The claimed subject matter is not limited to implementations that solve any or all disadvantages noted in the Background.

BRIEF DESCRIPTION OF THE DRAWINGS

FIG. 6 is a simplified isometric view of an electrode fastened to an electrically conductive wire in accordance with embodiments of the invention.

FIGS. 7 and 8 respectively are cross-sectional exploded and assembled views of the electrode of FIG. 6 taken generally along line 6-6, in accordance with embodiments of the invention.

DETAILED DESCRIPTION OF ILLUSTRATIVE EMBODIMENTS

Figure 1:
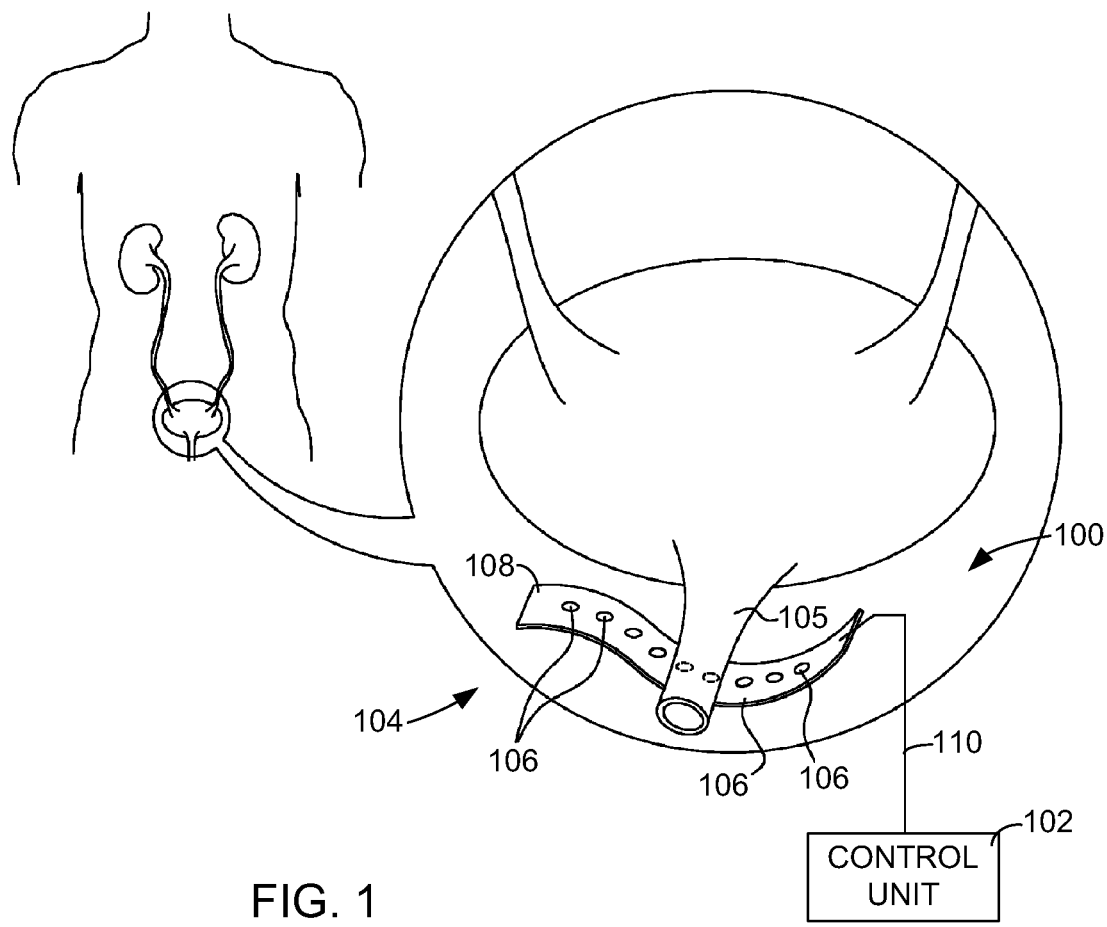
FIG. 1 is a schematic illustration of an exemplary electronic stimulator device having an electrode assembly formed in accordance with embodiments of the invention implanted around a urethra of a patient.

Embodiments of the invention are described more fully hereinafter with reference to the accompanying drawings. The various embodiments of the invention may, however, be embodied in many different forms and should not be construed as limited to the embodiments set forth herein. Rather, these embodiments are provided so that this disclosure will be thorough and complete, and will fully convey the scope of the invention to those skilled in the art. Elements that are identified using the same or similar reference characters refer to the same or similar elements.

It will be understood that when an element is referred to as being "connected" or "coupled" to another element, it can be directly connected or coupled to the other element or intervening elements may be present. In contrast, if an element is referred to as being "directly connected" or "directly coupled" to another element, there are no intervening elements present. As used herein, the term "mechanically coupled" or "mechanically fastened" is a technique of coupling elements without welding or soldering that utilizes cooperating members of the elements to physically join the elements together.

It will be understood that, although the terms first, second, etc. may be used herein to describe various elements, these elements should not be limited by these terms. These terms are only used to distinguish one element from another. Thus, a first element could be termed a second element without departing from the teachings of the present invention.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art, and will not be interpreted in an idealized or overly formal sense unless expressly so defined herein.

FIG. 1 is a schematic illustration of an exemplary electronic stimulator device 100 in accordance with embodiments of the invention. In one embodiment, the device 100 comprises a control unit 102, and an electrode assembly 104 formed in accordance with one or more embodiments described herein. The control unit 102 may be in the form of an implantable device powered by a battery, or an external device.

In one embodiment, the control unit 102 is a conventional device that generates current pulses for stimulation therapies that treat a condition of a patient. In one embodiment, the electrode assembly 104 is configured for implantation into a pelvic region of a patient and delivers current pulses generated by the control unit 102 to muscle tissue and/or nerves to control and/or treat a pelvic condition of the patient, such as pelvic pain, urinary incontinence, fecal incontinence, erectile dysfunction or other pelvic condition that may be treated through electrical stimulation. For instance, the electrode assembly 104 may be implanted adjacent the urethra 105 of a patient, such as illustrated in FIG. 1, to treat urinary incontinence. The assembly 104 may be implanted in other areas of the pelvic region to treat other conditions of the patient.

Figure 2:
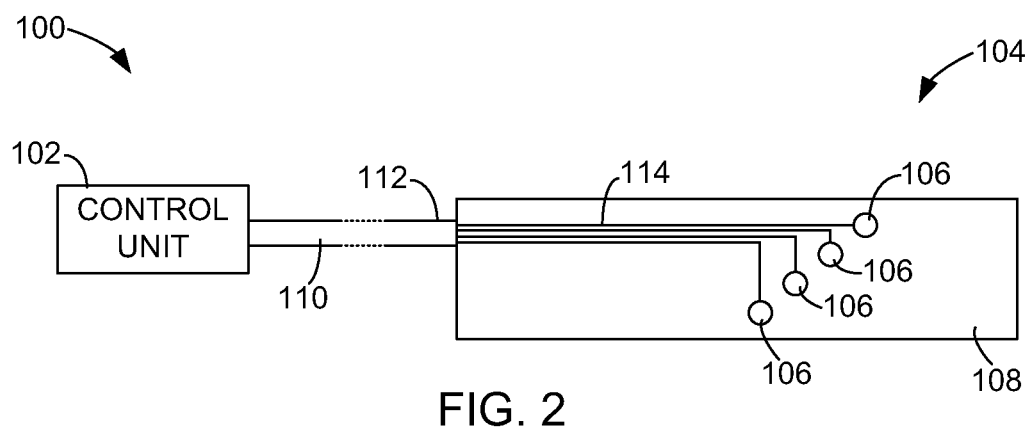
FIG. 2 is a schematic illustration of an electronic stimulator device including an electrode assembly formed in accordance with embodiments of the invention.

FIG. 2 is a schematic illustration of an electronic stimulator device 100 including an electrode assembly 104 formed in accordance with embodiments of the invention. In one embodiment, the electrode assembly 104 includes one or more electrodes 106 attached to mesh 108, which may be electrically coupled to the control unit 102 through an implantable lead 110. In one embodiment, the assembly 104 includes a connector (not shown) that attaches to a distal end 112 of the lead 110 and forms an electrical connection between one or more electrically conductive wires 114 of the assembly 104 that are coupled to the electrodes 106 and wires within the lead 110 that are coupled to the control unit 102. Thus, current pulses generated by the control unit 102 may be delivered to target tissue of the patient through the lead 110 and the electrodes 106.

In one embodiment, each of the electrodes 106 is coupled to the control unit 102 through a single conductive path. As a result, current pulses generated by the control unit 102 are delivered simultaneously to each of the electrodes 106 of the assembly 104.

In one embodiment, each of the electrodes 106, or subsets of the electrodes 106, are electrically coupled to the control unit 102 through different conductive paths. This allows the control unit 102 to apply different current pulses to different electrodes 106 or groups of electrodes 106, and apply the current pulses at different times. This feature can simplify the placement of the assembly 104 near the target site, as the electrodes 106 may be tested to determine which of the electrodes 106 is in the best position to apply the electrical stimulation therapy to the patient.

In one embodiment, the control unit 102 includes memory and a processor configured to execute a stimulation program stored in the memory. The stimulation program defines the current pulses to be applied to the electrodes 106, identifies the electrodes 106 that are to receive the current pulses, and defines a timing schedule that determines when the electrodes 106 receive the current pulses. The execution of the stimulation program by the processor causes the control unit 102 to deliver stimulation pulses to the electrodes in accordance with the stimulation program to treat a condition of the patient.

In one embodiment, the mesh 108 is flexible and configured to bend around the target site, such as around the urethra 105 of the patient, as shown in FIG. 1. Tissue ingrowth through the mesh 108 operates to anchor the electrodes 106 relative to the tissue, in which the mesh 108 is implanted. This prevents undesirable migration of the electrodes 106 relative to the tissue.

Figure 3:
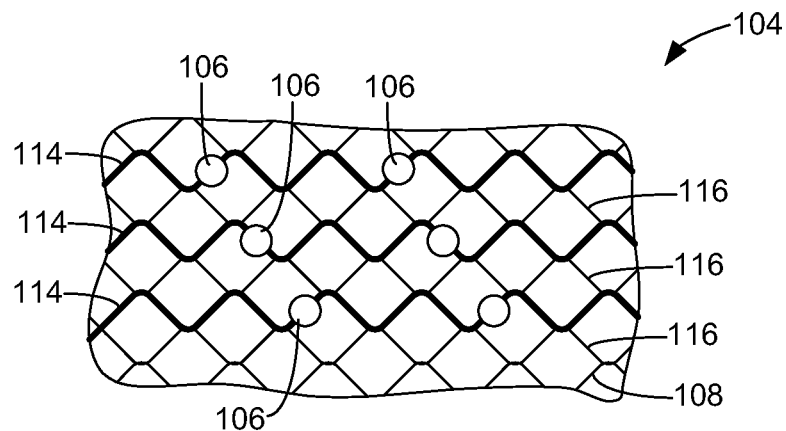
FIG. 3 is schematic illustration of a portion of an electrode assembly in accordance with embodiments of the invention.

FIG. 3 is a schematic illustration of a portion of the electrode assembly 104 in accordance with embodiments of the invention. In one embodiment, the mesh 108 comprises one or more of the electrically conductive wires 114. In one embodiment, the wires 114 are woven together to form the mesh. In one embodiment, the mesh 108 also includes electrically insulative or non-conducting fibers 116, such as fibers formed of polypropylene or other suitable biocompatible material. In one embodiment, the wires 114 are woven through the insulative fibers 116, as shown in FIG. 3. While the electrically conductive wires 114 are illustrated in FIG. 3 as generally extending in a single direction, electrically conductive wires 114 can be included in the mesh 108 that extend transversely to those illustrated in FIG. 3.

In one embodiment, the electrodes 106 are arranged in a desired pattern on the mesh 108. Thus, the electrodes 106 may be arranged in a line, an array, or other desired pattern.

Figure 4:
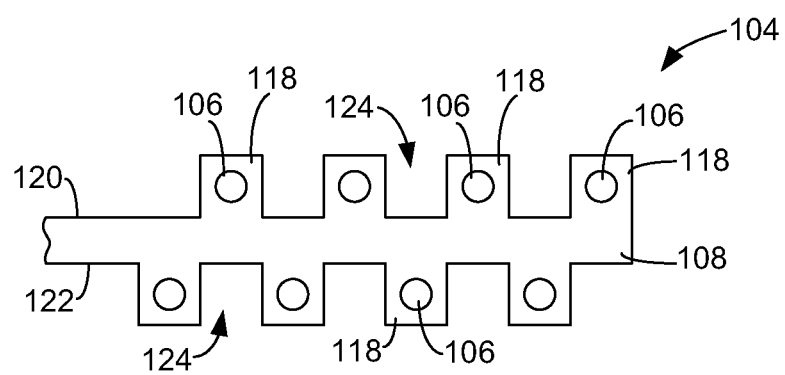
FIGS. 4 and 5 are schematic illustrations of an electrode assembly in accordance with embodiments of the invention.
Figure 5:
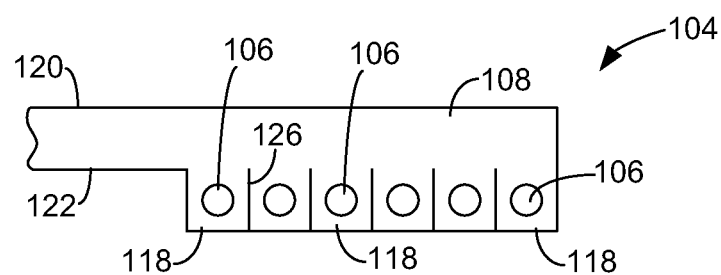

FIGS. 4 and 5 are schematic illustrations of the electrode assembly 104 in accordance with embodiments of the invention. Details of the mesh 108 are not shown in order to simplify the illustrations. In one embodiment, the mesh 108 includes tabs 118 that extend from an edge or side of the mesh 108. In one embodiment, the tabs 118 extend along opposing side edges 120 and 122 of the mesh 108, as shown in FIG. 4. In one embodiment, the tabs 118 extend from a single edge 122 of the mesh 108, as shown in FIG. 5.

In one embodiment, each of the plurality of tabs 118 are each separated from adjacent tabs 118 by a gap 124, as shown in FIG. 4. In one embodiment, at least some of the tabs 118 are separated from other portions of the mesh 108 on three sides, as shown in FIG. 4. This allows the tabs 118 to flex relative to other portions of the mesh 108 and provides a wide range of movement of the individual electrodes 106 that are attached to each of the tabs 118, and allows for additional adjustments to be made to the relative positions of the electrodes 106 to optimize the location of electrodes 106 within the target site.

In one embodiment, some of the tabs 118 adjoin adjacent tabs, as shown in FIG. 5. In one embodiment, the separation between adjacent tabs 118 is formed by a cut 126 in the mesh 108.

In one embodiment, the electrodes 106 are attached to the mesh 108 using a suitable adhesive or over-molding process. In one embodiment, each of the electrodes 106 is electrically coupled to one of the wires 114 using a conventional process, such as welding or soldering.

In accordance with one embodiment, the electrodes 106 are each mechanically coupled to one of the wires 114 of the mesh 108. FIG. 6 is a simplified isometric view of an exemplary electrode 106 that is mechanically fastened to an electrically conductive wire 114 in accordance with embodiments of the invention. In one embodiment, the electrode 106 includes members 130 and 132, and a stimulation surface 134, which is electrically coupled to the wire 114 responsive to the mechanical fastening of the members 130 and 132 together around the wire 114.

The mechanically fastened feature of the electrodes 106 allows for customized placement of the electrodes 106 on the mesh 108. For instance, the electrodes 106 can be coupled to a selection of the available tabs 118 of the mesh 108 (FIGS. 4 and 5), or the electrodes 106 may be arranged in a desired pattern over the mesh 108.

FIG. 7 is a cross-sectional exploded view of the exemplary electrode 106 depicted in FIG. 6 taken along line 6-6 that is positioned around an electrically conductive wire 114. FIG. 8 is a cross-sectional view of the electrode of FIG. 7 with the first and second members 130 and 132 mechanically fastened around the wire 114.

In one embodiment, the wire 114 comprises an electrically insulative jacket 136 surrounding an electrically conductive core 138. In one embodiment, the member 130 includes a piercing member 140 that is configured to pierce the insulative jacket 136 of the wire 114 when the members 130 and 132 are mechanically fastened together, as shown in FIG. 8. The piercing of the insulative member 136 by the piercing member 140 creates a conductive path between the electrically conductive core 138 of the wire 114 and the stimulation surface 134. As a result, current pulses generated by the control unit 102 that are transmitted through the wire 114 are delivered to the stimulation surface 134 through the conductive path formed by the piercing member 140.

In one embodiment, the piercing member 140 comprises an electrically conductive protrusion 142. As illustrated in FIGS. 7 and 8, one embodiment of the protrusion 142 is a conical member, a point of which is used to pierce the insulative jacket 136 and engage the electrically conductive core 138.

Figure 9:
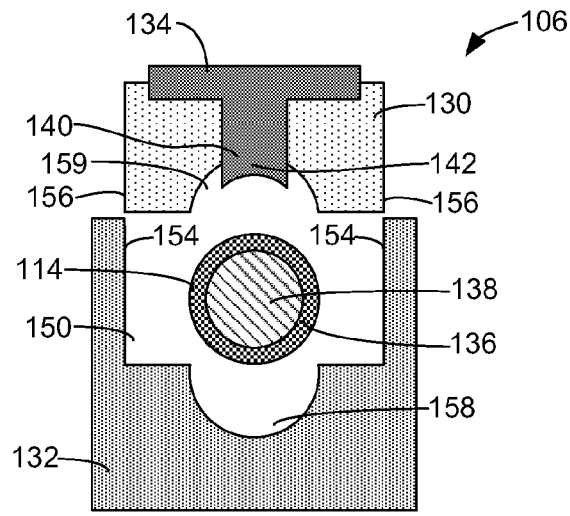
FIGS. 9 and 10 respectively are cross-sectional exploded and assembled views of the electrode of FIG. 6 taken generally along line 6-6, in accordance with embodiments of the invention.
Figure 10:
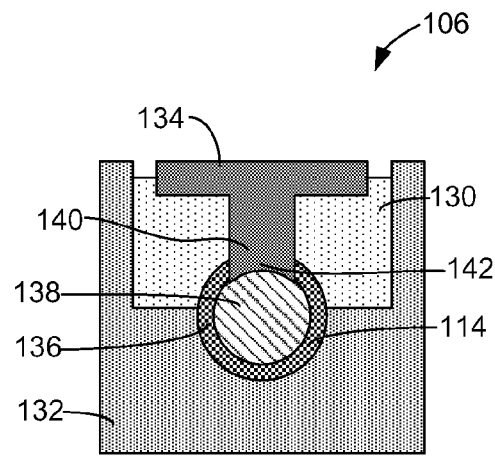

FIGS. 9 and 10 respectively are cross-sectional exploded and assembled views of the electrode of FIG. 6 taken generally along lines 6-6, in accordance with embodiments of the invention. In accordance with another embodiment, the protrusion 142 is in the form of a blade member, as shown in FIGS. 9 and 10. In one embodiment, the blade member form of the protrusion 142 slices through the insulative jacket 136 to contact the conductive core 138 and form the electrical connection between the conductive core 138 and the stimulation surface 134.

In one embodiment, the members 130 and 132 are mechanically fastened together around the wire using mechanical coupling. In one embodiment, the members 130 and 132 are fastened together by hand using the mechanical coupling.

In one embodiment, the mechanical coupling comprises cooperating portions of the members 130 and 132 that interface to fasten the members 130 and 132 together. In one exemplary embodiment, the member 132 includes arms 146 and 148 that define a recess 150 that is configured to receive the member 130, as shown in FIGS. 7 and 8. In one embodiment, the arms 146 and 148 flex to allow for the insertion of the member 130 within the recess 150. In one embodiment, the arms 146 extend over a top surface 152 of the member 130 to secure the member 130 within the recess 150, and provide a snap-fit connection. Other cooperating features of the members 130 and 132 may be used to provide a similar snap-fit connection and mechanically fasten the members 130 and 132 together.

In accordance with another embodiment, the mechanical coupling provides a press-fit connection (i.e., friction fit) between the first and second members 130 and 132. In one exemplary embodiment, the recess 150 of the member 132 is sized such that the sides 154 of the recess 150 interfere with the sides 156 of the member 130, as shown in FIGS. 9 and 10. When the member 130 is forced into the recess 150, the friction between the sides 154 and 156 fastens the members 130 and 132 together.

In one embodiment, at least one of the members 130 and 132 includes a wire guide that is configured to position the wire 114 in a predetermined location. In one embodiment, the wire guide is configured to promote the piercing of the insulative jacket 136 by the piercing member 140 when the members 130 and 132 are fastened together.

In one exemplary embodiment, the wire guide comprises a recess 158 that is formed in the member 132. The recess 158 is configured to position the wire in alignment with the piercing member 140, such that the piercing member 140 pierces the insulative jacket 136 of the wire 114 when the members 130 and 132 are mechanically fastened together, as shown in FIG. 8. In one embodiment, the member 130 includes a wire guide in the form of a recess 159, which operates to center the piercing member 140 over the wire 114 when the members 130 and 132 are fastened together.

Figure 11:
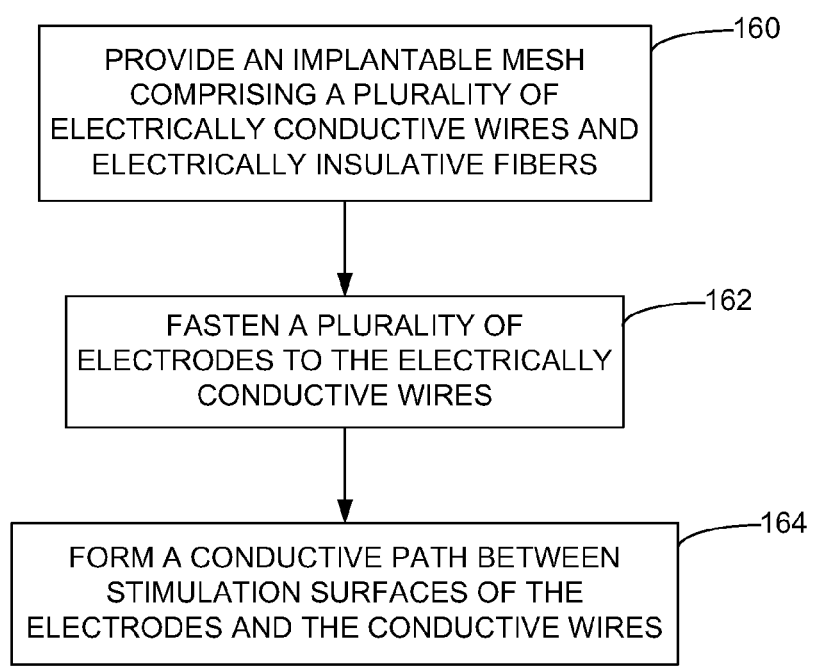
FIG. 11 is a flowchart illustrating a method in accordance with embodiments of the invention.

FIG. 11 is a flowchart illustrating a method in accordance with embodiments of the invention. At 160 of the method, an implantable mesh 108 is provided comprising a plurality of electrically conductive wires 114 and electrically insulative fibers 116, such as shown in FIG. 3.

At 162, a plurality of electrodes 106 are fastened to the electrically conductive wires 114. In one embodiment, the electrodes 106 are mechanically fastened to the electrically conductive wires through a mechanical coupling between members 130 and 132 of the electrodes 106. Exemplary embodiments of the mechanical coupling are discussed above with reference to FIGS. 6-10.

In one embodiment of step 162, portions of the members 130 and 132 are snap-fit together, as exemplified in FIGS. 7 and 8. In accordance with another embodiment, portions of the members 130 and 132 are press-fit together to fasten electrode 106 to the conductive wire 114, as exemplified in FIGS. 9 and 10.

At 164 of the method, a conductive path is formed between the stimulation surfaces 134 of the electrodes 106 and the conductive wires 114, to which they are attached. In one embodiment, the conductive path is formed responsive to the fastening step 162. In accordance with exemplary embodiments, one or both of the members 130 and 132 includes a piercing member 140 that pierces an insulative jacket 136 of the wire 114 and engages an electrically conductive core 138 of the wire 114, as shown in FIGS. 8 and 10. The engagement of the piercing member 140 with the electrically conductive core 138 provides a conductive path between the conductive core 138 and the stimulation surface 134 of the electrode 106.

In accordance with another embodiment of the method, the electrode assembly 104 formed of the mesh 108 and the fastened electrodes 106 is implanted in tissue of a patient. In one embodiment, the electrode assembly 104 is implanted within a pelvic region of a patient, such as around the urethra 105 (FIG. 1), or other location. In one embodiment, electrical stimulation signals are delivered to the tissue of the patient through the conductive wires 114 and one or more of the attached electrodes 106 to treat a condition of the patient, such as, for example, urinary incontinence, fecal incontinence, sexual dysfunction, pelvic pain due to interstitial cystitis, or other pelvic condition.

Although the present invention has been described with reference to preferred embodiments, workers skilled in the art will recognize that changes may be made in form and detail without departing from the spirit and scope of the invention.

What is claimed is:

1. An implantable electrode assembly for delivering electrical stimulation signals to tissue of a patient, the assembly comprising:
an implantable mesh comprising a plurality of electrically conductive wires; and
a plurality of electrodes, each electrode comprising first and second members fastened together around a segment of one of the electrically conductive wires using a mechanical coupling, the first member including a stimulation surface, and the second member including a first arm, a second arm, and a recess to receive the first member, the segment of the wire extending through the recess;
wherein:
an electrically conductive path is formed between the stimulation surface and the electrically conductive wire to which the first and second members are fastened; and
the mechanical coupling comprises cooperating portions of the first and second members that interface to fasten the first and second members together, the first arm and the second arm configured to flex to insert the first member within the recess such that the first member is disposed between the first arm and the second arm.

2. The assembly of claim 1, wherein:
the electrically conductive wires each comprise an electrically insulative jacket surrounding an electrically conductive core;
the first member comprises a piercing member that pierces the insulative jacket and contacts the conductive core of the wire, to which the first and second members are fastened; and
the piercing member forms a portion of the electrically conductive path.

3. The assembly of claim 2, wherein the piercing member comprises an electrically conductive protrusion.

4. The assembly of claim 3, wherein the protrusion comprises a conical member.

5. The assembly of claim 3, wherein the protrusion comprises a blade member.

6. The assembly of claim 2, wherein at least one of the first and second members comprises a wire guide configured to position the wire, around which the first and second members are fastened, in a predetermined location.

7. The assembly of claim 6, wherein the wire guide comprises a first guide wire recess in the first member, and a second guide wire recess in the second member, the second guide wire recess having a different size than the recess of the second member.

8. The assembly of claim 1, wherein the cooperating portions form a snap-fit connection between the first and second members.

9. The assembly of claim 1, wherein the cooperating portions form a press-fit connection between the first and second members.

10. The assembly of claim 1, wherein the implantable mesh comprises a plurality of tabs and each of the plurality of electrodes is fastened to one of the tabs.

11. The assembly of claim 10, wherein the tabs are formed along an edge of the mesh.

12. The assembly of claim 1, wherein each of the first arm and the second arm include a portion that extends over a surface of the first member.

13. A method comprising:
providing an implantable mesh comprising a plurality of electrically conductive wires; and
fastening a plurality of electrodes to the electrically conductive wires comprising mechanically fastening first and second members of each of the electrodes to a segment of one of the wires including interfacing cooperating portions of the first and second members, wherein the second member includes a first arm, a second arm, and a recess to receive the first member, the first arm and the second arm flexing to insert the first member within the recess such that the first member is disposed between the first arm and the second arm, the segment of the wire extending through the recess; and
forming a conductive path between stimulation surfaces on the first members of the electrodes and the conductive wires in response to fastening a plurality of electrodes to the electrically conductive wires.

14. The method of claim 13, wherein fastening a plurality of electrodes to the electrically conductive wires comprises piercing an insulative jacket of the wire with a piercing member of the electrode.

15. The method of claim 14, wherein mechanically fastening first and second members of each of the plurality of electrodes to one of the wires comprises press-fitting the cooperating portions of the first and second members together around the wire.

16. The method of claim 14, wherein mechanically fastening first and second members of each of the plurality of electrodes to one of the wires comprises snap-fitting the cooperating portions of the first and second members together around the wire.

17. The method of claim 13, further comprising:
implanting the mesh and the fastened electrodes in tissue of a patient; and
delivering electrical stimulation signals to the tissue of the patient through the conductive wires and the electrodes.

18. The method of claim 13, wherein the first member defines a first wire guide recess, the second member defines a second wire guide recess, and the mechanically fastening first and second members of each of the electrodes to a segment of one of the wires comprises positioning the first wire guide recess and the second wire guide recess around the segment of the wire.

* * * * *